(12) United States Patent
Chen

(10) Patent No.: US 7,929,747 B2
(45) Date of Patent: Apr. 19, 2011

(54) SYSTEM AND METHOD FOR ESTIMATING DATA MISSING FROM CT IMAGING PROJECTIONS

(75) Inventor: Guang-Hong Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 999 days.

(21) Appl. No.: 11/738,680

(22) Filed: Apr. 23, 2007

(65) Prior Publication Data
US 2007/0248255 A1 Oct. 25, 2007

Related U.S. Application Data

(60) Provisional application No. 60/794,684, filed on Apr. 25, 2006.

(51) Int. Cl.
G06K 9/00 (2006.01)
(52) U.S. Cl. ........................................................ 382/131
(58) Field of Classification Search .................. 382/128, 382/131; 378/4, 21, 25
See application file for complete search history.

(56) References Cited

U.S. PATENT DOCUMENTS

| | | | | |
|---|---|---|---|---|
| 5,253,171 | A * | 10/1993 | Hsiao et al. | 378/4 |
| 5,270,926 | A * | 12/1993 | Tam | 378/4 |
| 5,625,190 | A | 4/1997 | Crandall | |
| 5,848,114 | A * | 12/1998 | Kawai et al. | 378/4 |
| 6,148,056 | A | 11/2000 | Lin et al. | |
| 6,560,308 | B1 | 5/2003 | Zmora | |
| 6,771,732 | B2 * | 8/2004 | Xiao et al. | 378/4 |
| 6,845,143 | B2 * | 1/2005 | Gringauz et al. | 378/8 |
| 7,507,968 | B2 * | 3/2009 | Wollenweber et al. | 250/363.07 |
| 2002/0131549 | A1 * | 9/2002 | Oikawa | 378/19 |
| 2004/0146136 | A1 * | 7/2004 | Gringauz et al. | 378/4 |
| 2004/0179643 | A1 * | 9/2004 | Gregerson et al. | 378/4 |
| 2006/0062443 | A1 * | 3/2006 | Basu et al. | 382/131 |
| 2006/0257010 | A1 * | 11/2006 | George et al. | 382/131 |

OTHER PUBLICATIONS

Yuying et al. "A Computional Algorithm for minimizing Total variation in Image Restoration", IEEE Tarnscations on Image Processing, vol. 5, Issue 6, Jun. 1996.*
Vogel et al. "Fast, Robust Total Variation-Based Reconstruction of Noisy, Blured Images", IEEE Transactios on Image Processing, vol. 7, Issue 6, Jun. 1998.*
PCT International Search Report.

* cited by examiner

Primary Examiner — Brian Q Le
Assistant Examiner — Shervin Nakhjavan
(74) Attorney, Agent, or Firm — Quarles & Brady LLP

(57) ABSTRACT

A system and method for generating an image of an object that is substantially free of artifacts induced by missing data is disclosed. The method includes performing a computed tomography (CT) imaging process using a cone-beam traversed over an actual scan path to acquire actual CT data having missing data. The method also includes reconstructing an initial image of a volume of interest (VOI) using the actual CT data, with the initial reconstructed image having artifacts attributable to the missing data, and reprojecting the reconstructed image of the VOI onto a virtual scan path to at least acquire virtual data corresponding to the missing data. Further, the method includes reconstructing an improved image of the VOI using the actual CT data and the virtual data, with the artifacts reduced in the improved reconstructed image.

20 Claims, 6 Drawing Sheets

SYSTEM AND METHOD FOR ESTIMATING DATA MISSING FROM CT IMAGING PROJECTIONS

CROSS REFERENCE TO RELATED APPLICATION

This application is based on U.S. provisional patent application Ser. No. 60/794,684 filed Apr. 25, 2006 entitled "System and Method for Estimating Data Missing from CT Imaging Projections" and claims the benefit thereof.

BACKGROUND OF THE INVENTION

The present invention relates to computed tomography (CT) imaging apparatus, and more particularly, to image reconstruction methods.

In one current computed tomography system, an x-ray source emits a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce a transmission profile.

The source and detector array in a conventional CT system are rotated on a gantry or about a C-arm within the imaging plane and around the object so that the angle at which the x-ray beam intersects the object constantly changes. A group of x-ray attenuation measurements from the detector array at a given angle is referred to as a "view" and a "scan" of the object and comprises a set of views made at different angular orientations (θ) during one rotation of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a display.

Traditional 3D cone-beam CT systems often include curved detectors with multiple rows or flat-panel based area detectors so that the scanning path is a single circle or a single arc. In a 3D scan the x-ray beam diverges to form a cone beam that passes through the object and impinges on a two-dimensional array of detector elements. Each view is thus a 2D array of x-ray attenuation measurements and the complete scan produces a 3D array of attenuation measurements. These cone-beam CT systems have been widely used in diagnostic radiology where a multi-row detector is utilized, in interventional radiology where a flat-panel detector is mounted on a C-arm gantry to implement cone-beam CT, and in cone-beam CT image-guided radiation therapy where one or two flat-panel detectors are mounted on the slow gantry to perform cone-beam CT data acquisition.

However, the single circle/arc scanning path does not generate sufficient projections for a mathematically exact image reconstruction. In particular, due to the divergent paths followed by the x-ray beams, the data is incomplete or some data is "missed". Referring now to FIG. 1, an x-ray source 1 is directed toward an object 2 such that x-ray beams 3 impinge upon the object 2 on the way toward a detector array 4.

Referring to FIGS. 1 through 3, during an imaging process, the x-ray source 1 is rotated about a source trajectory 5 that is mirrored by the detector array 4. However, due to the diverging paths followed by the x-ray beams 3, no information is obtained about rotational axis 6 defined by the source trajectory 5. As such, although the object 2 of the imaging process has an oval shape, the beam paths represented in FIG. 2 only gather data along two circular cross-sectional areas separated by "missing data" 7. This missing data 7 is a problem that has historically plagued cone-beam CT data acquisition.

In particular, when an image is reconstructed using data with substantial missing data 7, artifacts are induced in the reconstructed image that significantly degrade the diagnostic quality of the image. That is, even if the area of the object 2 corresponding to the missing data 7 is not of diagnostic interest, the missing data 7 affects the overall quality of the image by inducing artifacts that can stray throughout the image.

To compensate for this missing data 7, many approximate image reconstruction methods have been developed for very small cone-angles (e.g., up to 5 degrees) as exemplified in U.S. Pat. Nos. 5,270,926; 6,104,775; 5,257,183; 5,625,660, 6,097,784; 6,219,441, and 5,400,255. However, when large cone-angles are used, such as in 128-slice helical CT imaging processes and flat-panel detector based cone-beam CT imaging processes, these approximate image reconstruction methods are insufficient to compensate for cone-beam artifacts caused by the missing data 7.

Therefore, it would be desirable to have a system and method for reconstructing data acquired using a cone-beam CT imaging process that has reduced artifacts and that is not limited by cone-angle, extended data acquisition processes, or overly cumbersome reconstruction algorithms.

SUMMARY OF THE INVENTION

The present invention overcomes the aforementioned drawbacks by providing a system and method for reconstructing an image using data acquired using a cone-beam CT imaging process that is substantially free of artifacts caused by missing data.

In accordance with one aspect of the invention, a method for generating an image of an object that is substantially free of artifacts induced by missing data includes performing a computed tomography (CT) imaging process using a cone-beam traversed over an actual scan path to acquire actual CT data having missing data. An image of a volume of interest (VOI) is reconstructed using the actual CT data to produce an initial reconstructed image which has artifacts attributable to the missing data. The initial reconstructed image can be updated or optimized using a total variation steepest descent method. The initial or updated reconstructed image of the VOI is then reprojected onto a virtual scan path to at least acquire virtual data corresponding to the missing data. Additionally, the method includes reconstructing an improved image of the VOI using the actual CT data and the virtual data with the artifacts attributable to the missing data reduced in the improved reconstructed image. The optimization step, reprojection step, and second reconstruction step can be performed in an iterative manner for a predetermined number of iterations or until the resultant reconstructed image meets a desired image quality metric.

In accordance with another aspect of the invention, a system for reconstructing CT images is disclosed that includes a computer that receives actual CT data from a CT system performing an imaging process using a cone-beam traversed over an actual scan path to acquire actual CT data having missing data. The system also includes a computer readable storage medium having stored thereon a computer program that, when executed by a processor of the computer, causes the computer to reconstruct an image of a VOI using the actual CT data, with the reconstructing image having artifacts attributable to the missing data. The processor operates to reproject the image of the VOI onto a virtual scan path to at least acquire virtual data corresponding to the missing data. Furthermore, the processor operates to reconstruct an improved image of the VOI using the actual CT data and the virtual data, with a reduction in artifacts attributable to the missing data.

Various other features and advantages of the present invention will be made apparent from the following detailed description and the drawings.

DETAILED DESCRIPTION OF THE PREFERRED EMBODIMENT

Figure 1:
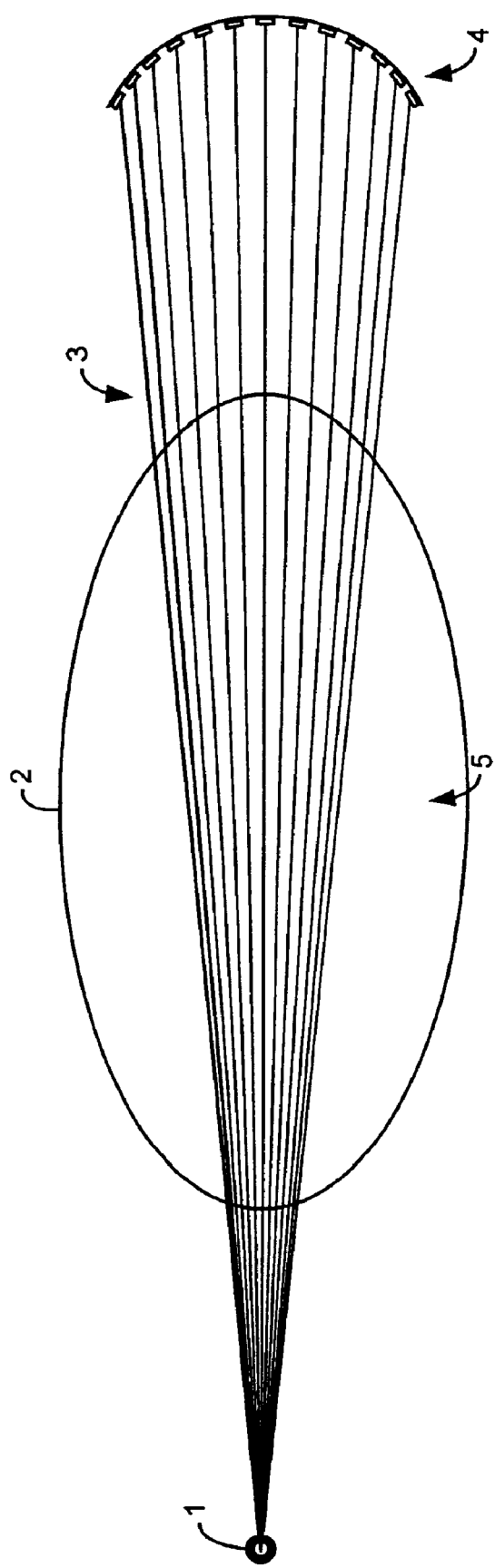
FIG. 1 is a pictorial view of a cone beam produced by a traditional CT imaging system impinging upon an imaging object.
Figure 2:
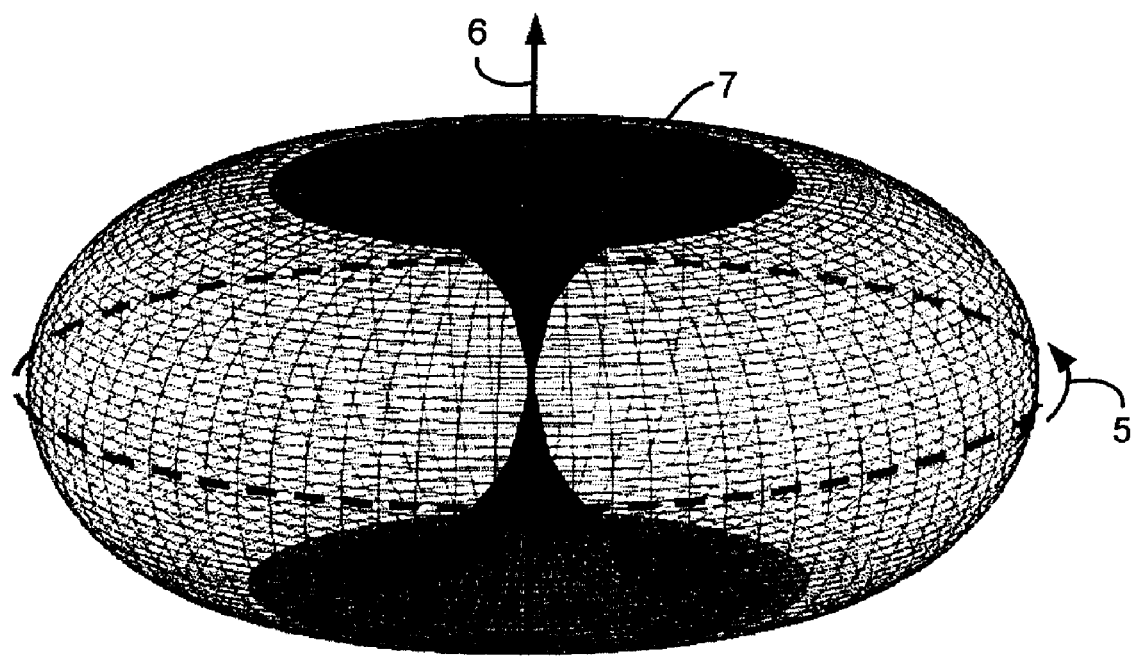
FIG. 2 is a pictorial view of trajectories produced by the cone beam of FIG. 1 when rotated about the imaging object.
Figure 3:
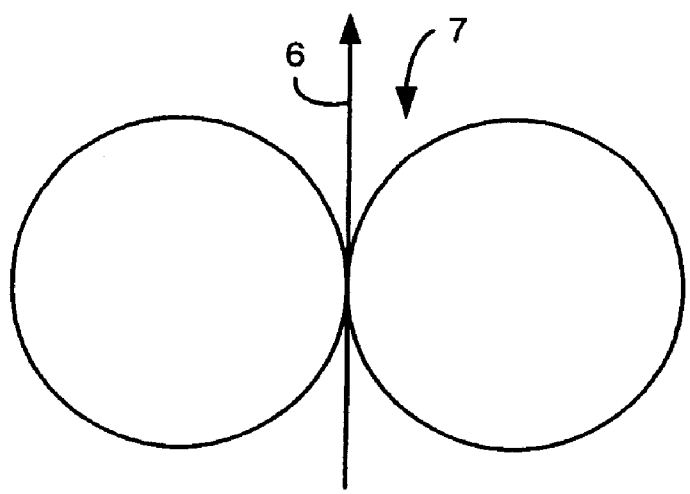
FIG. 3 is a pictorial view of one set of trajectories produced by the cone beam of FIG. 1 when rotated about the imaging object.
Figure 4:
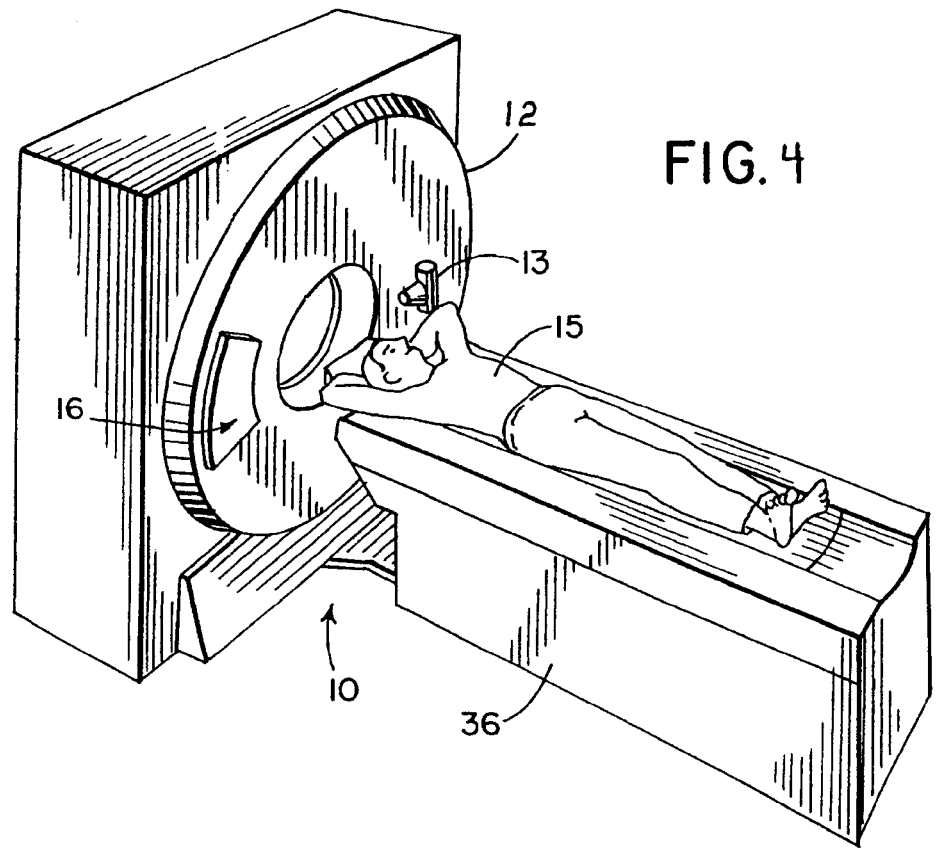
FIG. 4 is a pictorial view of a CT imaging system in which the present invention may be employed.
Figure 5:
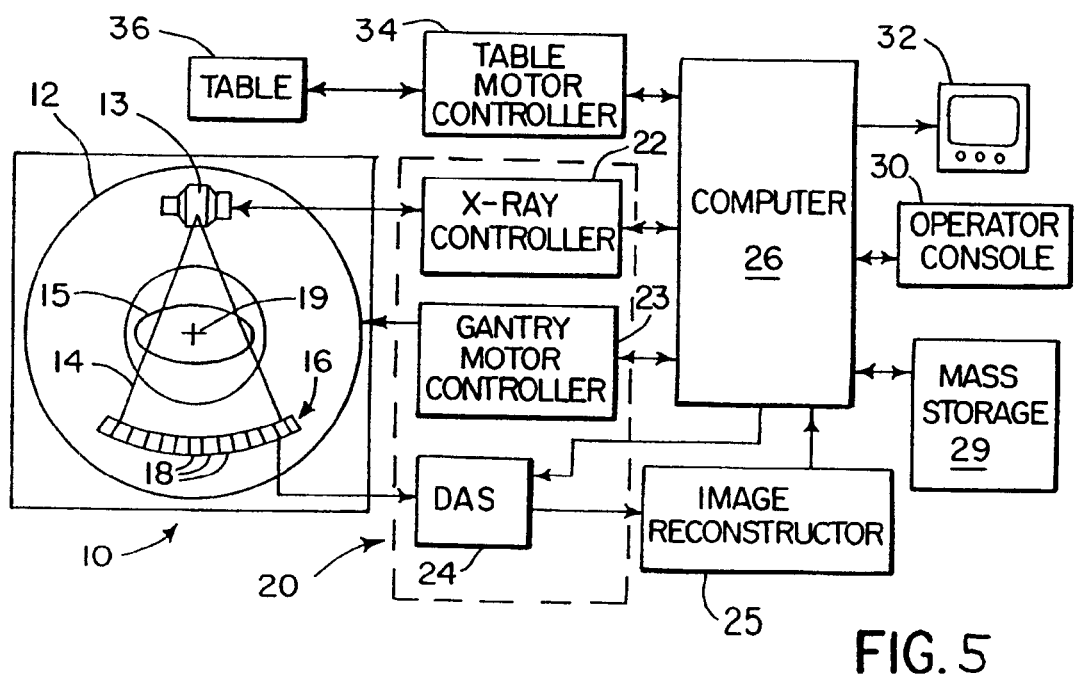
FIG. 5 is a block schematic diagram of the CT imaging system.

With initial reference to FIGS. 4 and 5, a computed tomography (CT) imaging system 10 includes a gantry 12 representative of a "third generation" CT scanner that includes a gantry 12. While the CT imaging system 10 is shown as including the gantry 12, it is also contemplated that the present invention may be used with CT systems employing a C-arm or other CT systems. In any case, the gantry 12 has an x-ray source 13 that projects a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry 12 and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25 receives sampled and digitized x-ray data from the DAS 24 and performs high speed image reconstruction according to the method of the present invention. The reconstructed image is applied as an input to a computer 26 which stores the image in a mass storage device 29.

The computer 26 also receives commands and scanning parameters, such as a scanning path, from an operator via console 30 that has a keyboard. An associated display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12. As will be described below, the present invention includes a system and method for estimating "missing data" or "missing projections" incurred in cone-beam CT imaging to generate images using the above-described cone-beam CT systems which are substantially free of artifacts introduced by missing data or missing projections.

Figure 6:
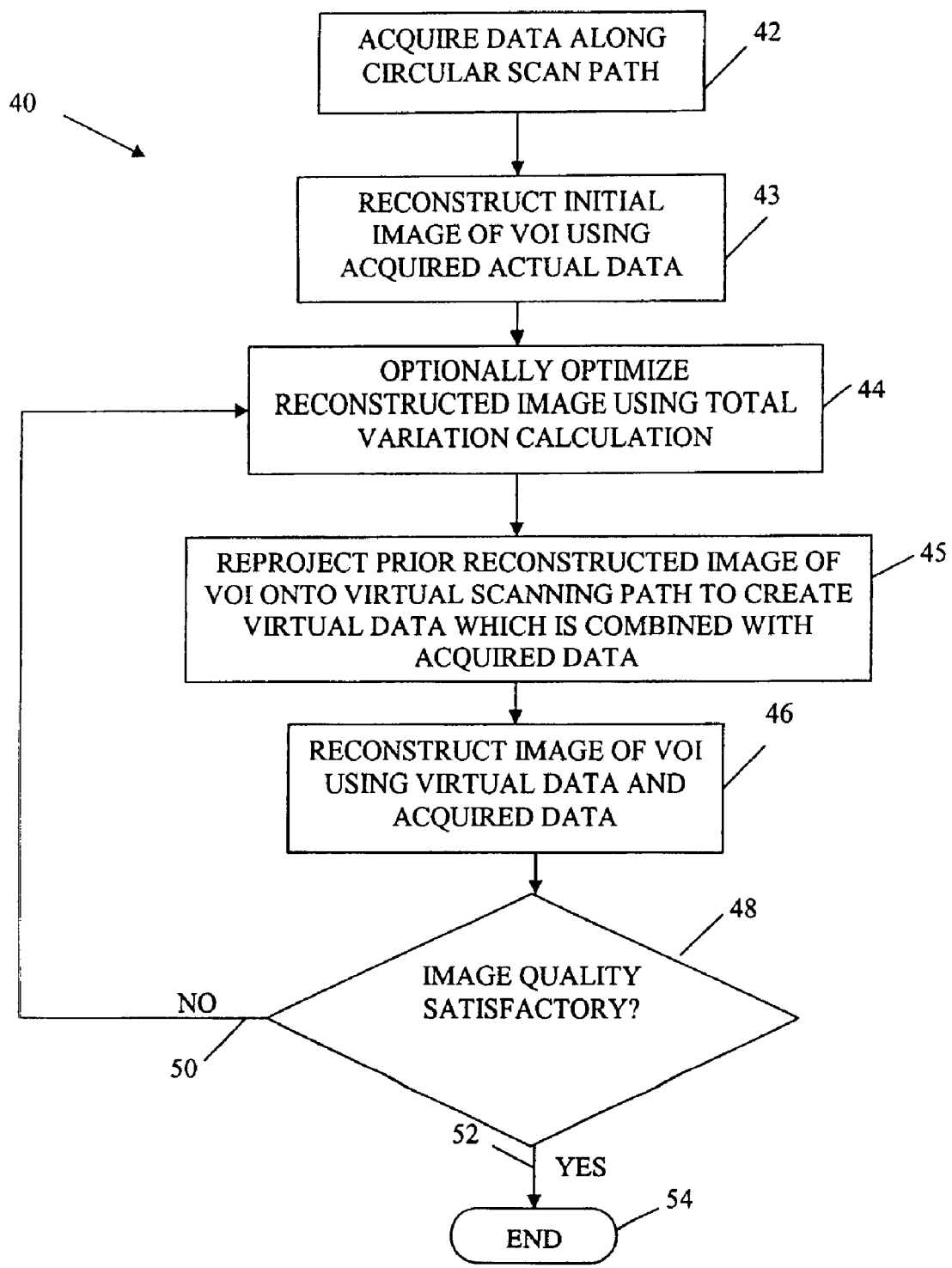
FIG. 6 is a flow chart setting forth the steps for processing data acquired using the CT system of FIGS. 4 and 5 to reconstruct an image substantially free of artifacts induced by missing data.
Figure 7:
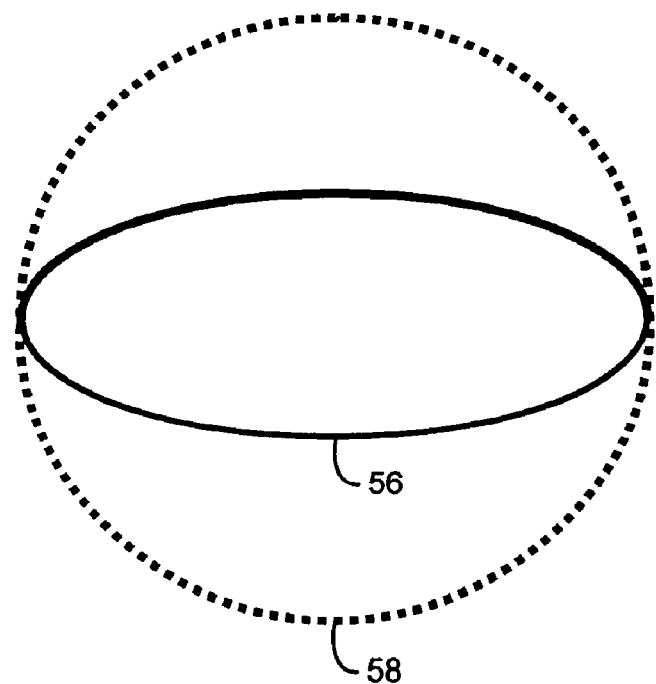
FIG. 7 is a pictorial view of a path followed by a cone beam produced by the CT imaging system of FIGS. 4 and 5 and an associated virtual scanning path used to reconstruct an image substantially free of artifacts induced by missing data.

Referring now to FIG. 6, the steps of a process 40 for reconstructing an image substantially free of artifacts induced by missing data begins by acquiring actual cone beam CT data along a circular scan path, as indicated at process block 42. The actual acquired data set is incomplete in that it does not include sufficient projection data for a mathematically exact reconstruction. Thus, the acquired actual CT data has missing data.

At process block 43, an initial image of a volume of interest (VOI) is reconstructed using the acquired data and a known image reconstruction method such as the Feldkamp's (FDK) image reconstruction method or another image reconstruction method. The resultant initial reconstructed image is based wholly on the incomplete acquired data obtained along the circular scan path and includes artifacts stemming from the missing data. As will be described, this initial reconstructed image of the VOI then serves as an initial seed image.

At process block 44, the reconstructed image of the VOI is optionally updated or optimized using some prior knowledge to produce an updated reconstructed image. During a first pass through process block 44, the initial reconstructed image can be updated, while in subsequent passes, an improved reconstructed image can be updated. In one embodiment, a total variation steepest descent calculation can be used to update each image voxel value in the reconstructed image.

The total variation (TV) of an image can be defined by:

$$TV = \sum_{m,n,o} \sqrt{\begin{array}{l}(f(m+1, n, o) - f(m, n, o))^2 + \\ (f(m, n+1, o) - f(m, n, o))^2 + \\ (f(m, n, o+1) - f(m, n, o))^2\end{array}}$$

where the summation is conducted over all the voxels of the image labeled by the indices (m,n,o), and f(m,n,o) denotes the corresponding image voxel value at voxel (m,n,o). Calculating the total variation of an image is one example of a metric which measures the quality of that image.

The gradient of the total variation, denoted by grad(TV), is calculated at each voxel of the reconstructed image, and the image value of each voxel of the reconstructed image is updated using the gradient at that voxel to produce an updated reconstructed image value using a steepest descent calculation or conjugate gradient method. For example, each voxel value $f_k(m,n,o)$ is updated to produce an updated voxel value $f_{k+1}(m,n,o)$ according to the following steepest descent calculation:

$$f_{k+1}(m,n,o) = f_k(m,n,o) - \alpha_k grad(TV)|_{(m,n,o)}$$

where $\alpha_k$ is a step length, which in a preferred embodiment is set to a constant.

Each voxel value of a reconstructed image may be updated using this total variation steepest descent calculation in an iterative manner for a predetermined number of iterations L. In a preferred embodiment, L is set to 20. In this manner, an updated reconstructed image can be obtained.

At process block 45, a reconstructed image of the VOI is reprojected to a virtual scanning path to obtain virtual data corresponding to the missing data. During a first pass through this process block, the updated reconstructed image is used in the reprojection, or if process block 44 is not performed, then the initial reconstructed image is used in the reprojection. As will be described below with respect to FIGS. 7 through 10, a virtual scanning path may take the form of a circle, a line, or an arc. Accordingly, a set of projections along a circle-plus-"circle," circle-plus-"line," or circle-plus-"arc" trajectory is formed by the reprojection step 44.

At process block 46, an improved image of the VOI is then reconstructed using the virtual data combined with the acquired actual data to generate an improved reconstructed image. That is, an improved image of the VOI is then reconstructed using an exact image reconstruction algorithm and the complete set of projections formed by the projection data originally acquired from the circular scan path at process block 42 as supplemented by the projection data calculated from the reprojected virtual scanning path. Note that the acquired actual CT data acquired from the actual circular scanning path is unchanged. Hence, the only added information is from the virtual scanning path created at process block 44 and the obtained virtual data. The improved reconstructed image has reduced artifacts compared to a prior reconstructed image of the VOI, e.g., compared to the initial reconstructed image which includes artifacts due to missing data.

In a preferred embodiment, an exact image reconstruction method can be used in process block 46 to generate the improved reconstructed image, such as the method described in U.S. Pat. No. 6,990,167, titled "Image Reconstruction Method for Divergent Beam Scanner", which is incorporated herein by reference. This method is preferred because it can be used with any x-ray source scan trajectory.

Once the new improved image is reconstructed using the virtual data and acquired actual data, the image quality is evaluated at process block 48. This evaluation may be performed in any of a variety of ways. For example, a physician or technician may simply review the reconstructed image to determine whether the current image is sufficiently free of artifacts. On the other hand, it is contemplated that this evaluation process 48 may be performed automatically as part of the image reconstruction process. For example, it is contemplated that latest reconstructed image of the VOI may be compared with the prior reconstructed image (initial or updated). In this case, each newly reconstructed image is compared to the previous image to determine whether the current improvement in the image is sufficient or whether further iterations are needed. Put another way, a threshold may be set that can be automatically used to determine whether the return (i.e. increase in image quality over the previous iteration) has diminished below the preset threshold and the iteration process should be discontinued.

In a preferred embodiment, at process block 48, it is determined whether the total variation of the latest reconstructed image is below a predetermined value. In each pass the total variation of the reconstructed image should be smaller than a total variation of a prior reconstructed image. Thus, at process block 48, a total variation is calculated of the reconstructed image generated at process block 46, and can be compared to a calculated total variation of a prior reconstructed image, such as one generated at process block 45.

If the total variation is not below the predetermined value, as indicated at 50, then processing proceeds to process block 44, and process blocks 44, 45, and 46 are repeated as many times as necessary. Specifically, again process block 44 is optional. Further, in subsequent passes at process block 45, the improved reconstructed image of the VOI is reprojected onto the virtual scanning path to create new virtual data. The new virtual data in combination with the actual acquired data forms a complete projection data set which is then used to reconstruct another improved image of the VOI at process block 46, and the image quality is again reviewed at process block 48.

Once the image quality is deemed sufficient as indicated at 52, preferably by determining that the total variation is below the predetermined value, the process is complete as indicated by process block 54.

Figure 8:
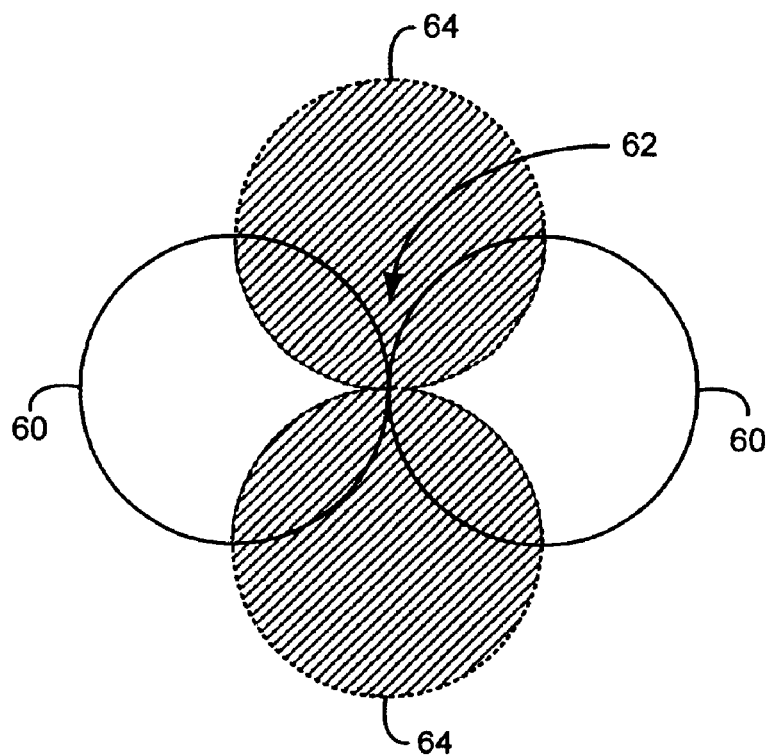
FIG. 8 is a pictorial view of data trajectories associated with the path followed by the actual cone-beam and an associated virtual scanning path of FIG. 7.
Figure 9:
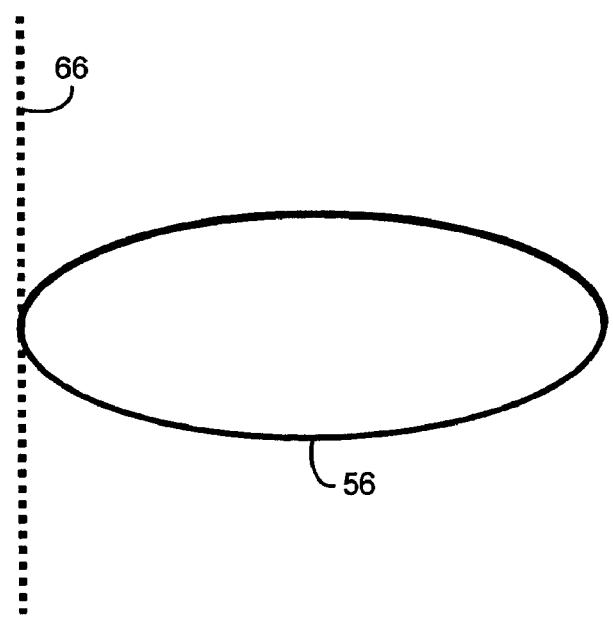
FIG. 9 is a pictorial view of a path followed by a cone beam produced by the CT imaging system of FIGS. 4 and 5 and an associated virtual scanning path used to reconstruct an image substantially free of artifacts induced by missing data.

In order to improve the signal-to-noise ratio (SNR) and reduce the required radiation dose, it is contemplated that the virtual scanning path is a circle. Hence, the complete scanning path is a circle-plus-(virtual)-circle, where an equal weighting scheme is used to reconstruct an image. For example, referring to FIG. 7 an actual scanning path indicated at 56 followed by a cone beam is circular and the virtual scanning path as indicated at 58 is a circle oriented orthogonal to the scanning path 56. As shown in FIG. 8, the Radon space data 60 acquired by the actual scanning path 56 has missing Radon space data indicated at 62. However, the virtual Radon space data 64 corresponding to the virtual scanning path 58 fill the areas of missing data 62 to create a "compete" set of data. Thus, when the complete data is reconstructed, the missing data 62 has been filled so that any artifacts that would have been induced by the missing data 62 are reduced or substantially eliminated.

Figure 10:
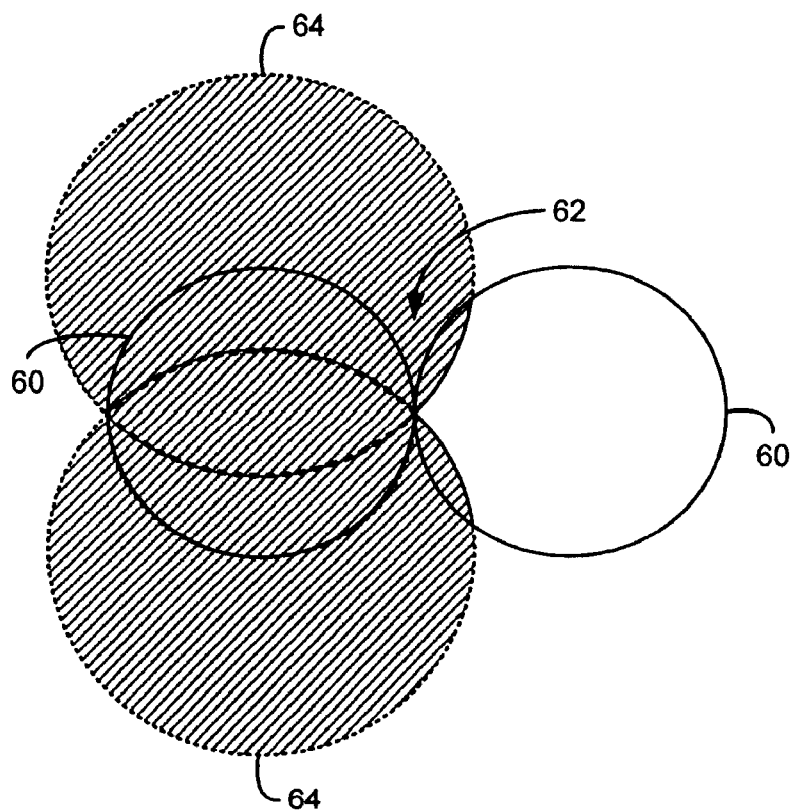
FIG. 10 is a pictorial view of data trajectories associated with the path followed by the actual cone-beam and another associated virtual scanning path of FIG. 9.

While a circle-plus-circle virtual complete scanning path is preferable to improve the signal-to-noise ratio (SNR) and reduce the required radiation dose, it is contemplated that the virtual complete scanning path may be a circle-plus-arc or circle-plus-line. For example, referring to FIG. 9, the actual scanning path 56 is again a circle. However, the virtual scanning path is a line 66. As shown in FIG. 10, when the virtual complete scanning path is a circle-plus-line, the Radon space data 64 corresponding to the virtual scanning path (line) 66 still fill the areas of missing data 62 to create a "compete" set of data. However, in order to acquire sufficient information to reproject the image of the VOI using a line or even arc, the actual dose used when acquiring data along the scanning path 56 must be increased over the above-described method using a circle-plus-circle virtual complete scanning path.

Therefore, the above-described system and method provides a new way to estimate virtual data (i.e. missing data or projections) to generate images that are substantially free of artifacts attributable to such missing data. In particular, data acquired using a cone-beam CT imaging process is reconstructed into an image of a VOI and then reprojected along a virtual path designed to elicit Radon space data within the areas of missing data. This process of reconstruction and reprojection can then be iteratively performed until an image substantially free of artifacts induced by missing data is reconstructed.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for generating an improved image of an object which is substantially free of artifacts induced by missing data comprising the steps of:
   a) performing a computed tomography (CT) image acquisition of the object using a cone-beam traversed over an actual scan path to acquire actual CT data which is incomplete and has missing data;
   b) reconstructing an initial image of a volume of interest (VOI) using the actual CT data, the initial reconstructed image having artifacts attributable to the missing data;
   c) reprojecting the reconstructed image of the VOI onto a virtual scan path to at least acquire virtual data corresponding to the missing data; and
   d) reconstructing an improved image of the VOI using the actual CT data and the virtual data, the improved reconstructed image having reduced artifacts compared to the initial reconstructed image of the VOI.

2. The method of claim 1 wherein the virtual scan path is orthogonal to the actual scan path.

3. The method of claim 1 wherein the actual scan path is a circle and the virtual scan path is one of a circle, an arc, and a line.

4. The method of claim 1 wherein the actual scan path is a circle and the virtual scan path is one of a circle, an arc, and a line and is orthogonal to the actual scan path.

5. The method of claim 1 further including calculating an updated reconstructed image from the initial reconstructed image and using the updated reconstructed image in step c).

6. The method of claim 1 further including calculating an updated reconstructed image from the initial reconstructed image using a total variation steepest descent calculation, and using the updated reconstructed image in step c).

7. The method of claim 1 further including:
   e) determining whether an image quality of the improved reconstructed image is satisfactory; and
   f) if the image quality is not satisfactory, then repeating step c) using the improved reconstructed image and repeating steps d) and e) until the image quality is satisfactory.

8. The method of claim 7, wherein step e) includes determining whether a total variation of the improved reconstructed image is less than a predetermined value.

9. The method of claim 1 further comprising:
   e) determining whether a reduction in artifacts between an improved reconstructed image and a prior reconstructed image is less than a predetermined threshold; and
   f) if the reduction in artifacts is not less than a predetermined threshold, then repeating step c) using the improved reconstructed image and repeating steps d), and e) until the reduction in artifacts is less than a predetermined threshold.

10. A method for generating an improved image of an object that is substantially free of artifacts induced by missing data comprising the steps of:
    a) performing a computed tomography (CT) image acquisition of the object using a cone-beam traversed over an actual scan path to acquire actual CT data which is incomplete and has missing data;
    b) reconstructing an initial image of a volume of interest (VOI) using the actual CT data, the initial reconstructed image having artifacts attributable to the missing data;
    c) updating the reconstructed image using a total variation steepest descent calculation;
    d) reprojecting the updated reconstructed image of the VOI onto a virtual scan path to at least acquire virtual data corresponding to the missing data;
    e) reconstructing an improved image of the VOI using the actual CT data and the virtual data, the improved reconstructed image having reduced artifacts compared to the initial reconstructed image of the VOI;
    f) determining whether an image quality of the improved reconstructed image is satisfactory; and
    g) if the image quality is not satisfactory, then repeating step c) using the improved reconstructed image, and repeating steps d), e) and f) until the image quality is satisfactory.

11. The method of claim 10 wherein the total variation steepest descent calculation includes defining the total variation (TV) by:

$$TV = \sum_{m,n,o} \sqrt{\begin{array}{l}(f(m+1, n, o) - f(m, n, o))^2 + \\ (f(m, n+1, o) - f(m, n, o))^2 + \\ (f(m, n, o+1) - f(m, n, o))^2\end{array}}$$

where f(m,n,o) is the corresponding image voxel value at a voxel labeled by indices (m,n,o), and each voxel value $f_k$(m,n,o) is updated to produce an updated voxel value $f_{k+1}$ (m,n,o) according to the following:

$f_{k+1}$(m,n,o) = $f_k$ (m, n, o) − $\alpha_k$grad(TV)$|_{(m,n,o)}$, where $\alpha_k$ is a steplength and is a predetermined constant.

12. The method of claim 10 wherein the virtual scan path is orthogonal to the actual scan path.

13. The method of claim 10 wherein the actual scan path is a circle and the virtual scan path is one of a circle, an arc, and a line.

14. The method of claim 10 wherein the actual scan path is a circle and the virtual scan path is one of a circle, an arc, and a line and is orthogonal to the actual scan path.

15. The method of claim 10, wherein step f) includes determining whether a total variation of the improved reconstructed image is less than a predetermined value.

16. A system for reconstructing CT images of an object comprising:
    a computer that receives actual CT data from a CT system performing an imaging process of an object using a cone-beam traversed over an actual scan path to acquire actual CT data having missing data;
    a computer readable storage medium having stored thereon a computer program that, when executed by a processor of the computer, causes the computer to:

reconstruct an initial image of a VOI using the actual CT data, the initial reconstructed image having artifacts attributable to the missing data;

reproject the reconstructed image of the VOI onto a virtual scan path to at least acquire virtual data corresponding to the missing data; and reconstruct an improved image of the VOI using the actual CT data and the virtual data, the improved reconstructed image having reduced artifacts compared to the initial reconstructed image of the VOI.

17. The system of claim 16 wherein the virtual scan path is at least one of a circular scan path, an arcuate scan path, and a linear scan path.

18. The system of claim 16 wherein the processor is further caused to select the virtual scan path to be orthogonal to the actual scan path.

19. The system of claim 16 wherein the processor is further caused to reconstruct images of the VOI using the actual CT data and virtual data using an exact image reconstruction algorithm.

20. The system of claim 16 wherein the processor is further caused to iteratively reproject a prior reconstructed image of the VOI onto the virtual scan path to acquire new virtual data and then reconstruct an image of the VOI using the actual CT data and the new virtual data until an image quality is satisfactory.

* * * * *